(12) United States Patent
Polzin et al.

(10) Patent No.: US 7,929,144 B1
(45) Date of Patent: Apr. 19, 2011

(54) OPTICAL SYSTEM AND METHOD FOR GAS DETECTION AND MONITORING

(75) Inventors: Kurt A. Polzin, Owens Cross Roads, AL (US); Valentin Korman, Huntsville, AL (US); William K. Witherow, Huntsville, AL (US); Adam Gail Hendrickson, Madison, AL (US); John Elihu Sinko, Oberlin, OH (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 336 days.

(21) Appl. No.: 12/336,260

(22) Filed: Dec. 16, 2008

(51) Int. Cl.
G01B 9/02 (2006.01)

(52) U.S. Cl. ........................ 356/477; 356/480

(58) Field of Classification Search .................. 356/451, 356/454, 477, 480, 519
See application file for complete search history.

(56) References Cited

U.S. PATENT DOCUMENTS

| | | | |
|---|---|---|---|
| 4,404,843 A | 9/1983 | Johnson et al. | |
| 4,862,731 A | 9/1989 | Gates | |
| 5,647,435 A | 7/1997 | Owens et al. | |
| 5,862,670 A | 1/1999 | Lak | |
| 6,178,754 B1 | 1/2001 | Dujarric | |
| 6,240,785 B1 | 6/2001 | Chapman et al. | |
| 6,374,618 B1 | 4/2002 | Lak | |
| 6,701,776 B2 | 3/2004 | Stetter | |
| 6,854,320 B2 | 2/2005 | Wolford et al. | |
| 6,886,389 B1 | 5/2005 | Hagar | |
| 7,000,456 B2 | 2/2006 | Lehmann | |
| 7,012,696 B2 * | 3/2006 | Orr et al. | 356/454 |
| 7,168,297 B2 | 1/2007 | Herzog et al. | |
| 2007/0000310 A1 | 1/2007 | Yamartino et al. | |
| 2010/0014094 A1 * | 1/2010 | Cole et al. | 356/480 |

OTHER PUBLICATIONS

J. Sinko, V. Korman, A. Hendrickson, & K.A. Polzin, An Interferometric Sensor for Detection of Gas Leaks in a Vacuum Environment, 4th Liquid Propulsion Subcommittee Mtg./JANNAF Interagency Propulsion Committee, Dec. 8, 2008, pp. 1-6, Orlando, FL.

* cited by examiner

*Primary Examiner* — Michael A Lyons
(74) *Attorney, Agent, or Firm* — Peter J. Van Bergen; James J. McGroary

(57) ABSTRACT

A free-space optical path of an optical interferometer is disposed in an environment of interest. A light beam is guided to the optical interferometer using a single-mode optical fiber. The light beam traverses the interferometer's optical path. The light beam guided to the optical path is combined with the light beam at the end of the optical path to define an output light. A temporal history of the output light is recorded.

28 Claims, 3 Drawing Sheets

OPTICAL SYSTEM AND METHOD FOR GAS DETECTION AND MONITORING

ORIGIN OF THE INVENTION

The invention described herein was made in the performance of work under a NASA contract and by an employee of the United States Government and is subject to the provisions of Public Law 96-517 (35 U.S.C §202) and may be manufactured and used by or for the Government for governmental purposes without the payment of any royalties thereon or therefore. In accordance with 35 U.S.C §202, the contractor elected not to retain title.

BACKGROUND OF THE INVENTION

1. Field of the Invention

This invention relates to gas detection and monitoring. More specifically, the invention is an optical-based system and method for detecting and monitoring the presence of gas in vacuum environments such as space.

2. Description of the Related Art

In terms of near-term, long-distance space travel, missions to the Moon and Mars are likely possibilities. Lunar and longer-term Martian missions may require the capability to store cryogenic liquids in an unmanned state for long periods of time. Storage containers filled with cryogenic fluids, helium pressurant, or methane propellant, could be placed on the lunar surface in advance of a manned landing. Earth Departure Stages (EDS) for trips to the moon and Mars could be "parked" in orbit for several months with the tanks thereof being maintained in a filled state. A method for determining whether these pressurized systems are in a 'safe' (i.e., non-leaking) condition is needed before resources are allocated for a rendezvous with a space crew. Furthermore, during the course of a mission, it becomes critical to monitor the system's health to ensure that no leaks develop and/or discover them early after their occurrence so corrective measures can be taken before the mission is endangered.

Since space environments are essentially vacuum environments, any leak detection and/or monitoring system/method must be capable of operating in a vacuum environment. In general, there are several methods to detect the presence of a gas in vacuum, but no off-the-shelf instrument is particularly well-suited as a candidate for leak detection that can occur on various times scales and lead to pressure levels in the vicinity of the leak that span several orders of magnitude. High-vacuum gauges (ion gauges) are quite accurate at low pressures, but they are relatively fragile and their filaments can become damaged if operation is attempted above 1 milliTorr for any prolonged period of time. Furthermore, high-vacuum gauges generate heat that could ignite a leaking combustible propellant. Mass spectrometers can be large and are difficult to locate in space-limited or remote locations. In addition, their operation requires high-voltage, the presence of which is generally not desirable next to a liquid hydrogen or oxygen tank. Reactive coupons (e.g., palladium-catalyzed silicon carbide) are generally species specific and can severely outgas in a vacuum environment to the point of uselessness. Several techniques to measure the amount of liquid in a cryogenic tank have been attempted or proposed, but none have been completely successful and most have fairly poor resolution. The sensitivity of these techniques does not allow detection of small leaks, or identification of the leak location.

SUMMARY OF THE INVENTION

Accordingly, it is an object of the present invention to provide a method and system for detecting and monitoring the presence of a gas in an environment of interest.

Another object of the present invention is to provide a method and system for detecting and monitoring gas leaks in vacuum or space environments.

Still another object of the present invention is to provide a method and system for detecting and monitoring gas leaks from spaced-based storage tanks.

Other objects and advantages of the present invention will become more obvious hereinafter in the specification and drawings.

In accordance with the present invention, a system and method are provided for detecting and monitoring the presence of a gas. A free-space optical path of an optical interferometer is disposed in an environment of interest. A light beam is guided to the optical interferometer using a single-mode optical fiber where the light beam traverses along the interferometer's optical path to an end thereof. The light beam guided to the optical path is combined with the light beam at the end of the optical path to define an output light. This output light is guided to an optical detector. A temporal history of the output light is recorded.

BRIEF DESCRIPTION OF THE DRAWING(S)

Other objects, features and advantages of the present invention will become apparent upon reference to the following description of the preferred embodiments and to the drawings, wherein corresponding reference characters indicate corresponding parts throughout the several views of the drawings and wherein.

DESCRIPTION OF THE PREFERRED EMBODIMENT(S)

Figure 1:
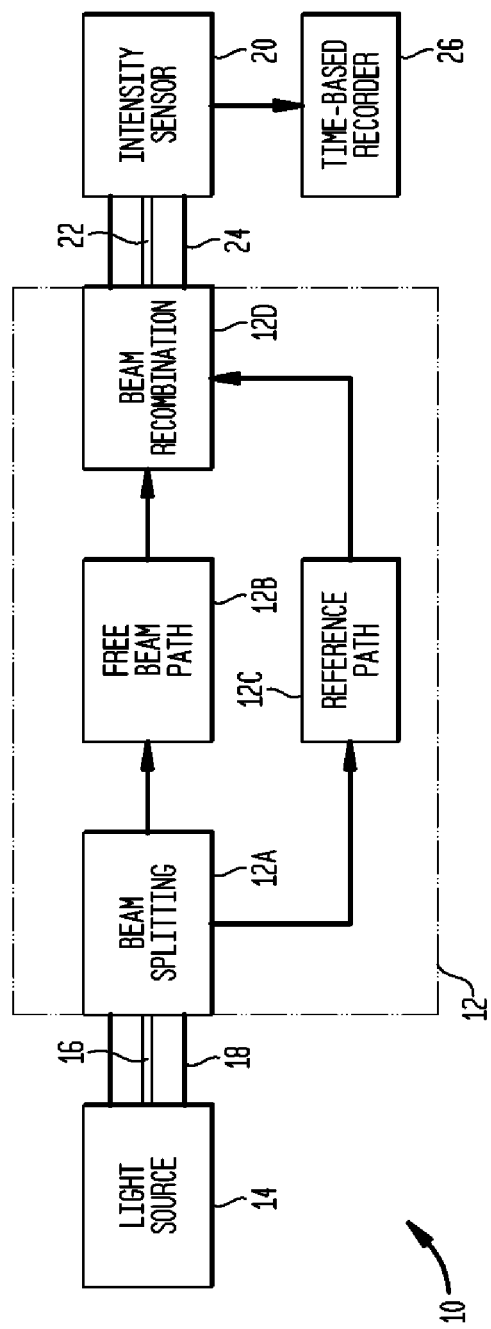
FIG. 1 is a block diagram of a gas detection and monitoring system in accordance with the present invention.

Referring now to the drawings and more particularly to FIG. 1, a block diagram of gas detection and monitoring system in accordance with an embodiment of the present invention is shown and is referenced generally by numeral 10. By way of illustrative example, the various embodiments of the present invention will be described for its use in detecting/monitoring the leakage of a gas into a non-gaseous vacuum environment. The gas would typically be stored in a positive-pressure container. For example, the container could be a cryogenic liquid storage tank parked in a spatial orbit or deployed on a lunar or other planetary surface. In either of these situations, it is assumed that the environment surrounding the storage tank is a non-gaseous space environment.

At the heart of system 10 is an optical interferometer 12 positioned where gas detecting/monitoring is of interest. Interferometer 12 can be constructed in accordance with the operating principles associated with a Fabry-Perot interferometer, a Mach-Zehnder interferometer, or a Michelson interferometer. By way of a non-limiting example, a flat and compact Michelson interferometer constructed in accordance with solid-body optics principles will be described later herein.

Regardless of the particular construction of interferometer 12, the operating principles of the present invention remain the same. At the front end of interferometer 12 of the illustrated embodiment, an incoming beam of light experiences beam splitting 12A in order to provide the light to a free beam path 12B and a reference path 12C. Free beam path 12B is an optical path defined by interferometer 12 that passes through free space and is exposed to the surrounding environment of interest (e.g., the space environment at a position of interest near a storage tank such as a cryogenic liquid storage tank). Reference path 12C is an optical path defined within interferometer 12 and is isolated from the surrounding environment. At the end of free beam 12B, the light beam passing therealong is combined with the light beam exiting reference path 12C at beam recombination 12D. The natural interference occurring from these two light beams serves as the output of interferometer 12.

The light provided to optical interferometer 12 originates at a light source 14 capable of generating a continuous beam of light with sufficient power to satisfy the operating principles of the present invention. For example, light source 14 can be a continuous wave (CW) laser (e.g., a helium-neon laser). A CW laser outputs energy in a form that is similar to a standing wave. Interferometer 12 splits the CW wave into two paths with one path being shifted relative to the other when there is interaction with the gas from a leak. When interferometer 12 then brings the two paths back together, interference occurs based on the relative optical phase difference between the two waves. It is to be understood that the present invention is not limited to use with a CW laser as a light emitting diode (LED) might also be suitable for certain low-power applications.

The light beam from source 14 is transmitted to interferometer 12 using a single-mode optical fiber 16. The single-mode fiber allows only one wave mode (e.g., the fundamental mode) to travel through the fiber. This maintains the coherence of the light. In this way, the ultimate interference generated by the optical interferometer will occur in the single mode thereby making it easier to measure.

Since light transmitted in an optical fiber can be affected by vibrations, the orientation of fiber 16 can be fixed by a "housing" 18 that can be realized in a variety of ways as would be understood by one of ordinary skill in the art. Accordingly, the particular nature and/or configuration of housing 18 are not limitations of the present invention.

As mentioned above, the output light generated by interferometer 12 is a natural interference between the light beam at the end of free beam path 12B and the light beam exiting reference path 12C. The intensity of this output light is detected at an intensity sensor 20 that is coupled in an optical sense to interferometer 12. For example, sensor 20 can be coupled directly to interferometer 12 or located remotely with respect thereto. Given the harshness of space environments, it may be desirable to locate sensor 20 in a protected environment. In such a case, a single-mode optical fiber 22 can be used to guide the output light from interferometer 12 to sensor 20. Similar to optical fiber 16, a housing 24 can be used to fix the orientation of optical fiber 22.

Since the goal of system 10 is to detect and monitor a gas presence, a time-based recorder 26 is coupled to intensity sensor 20. Recorder 26 is any suitable data recording device/system capable of recording the sensed data over a time period of interest. Since the intensity data is indicative of an amount of a gas, recording this data over time in a leak detection application provides an indication of a leak's starting point in time, duration, and severity.

Figure 2:
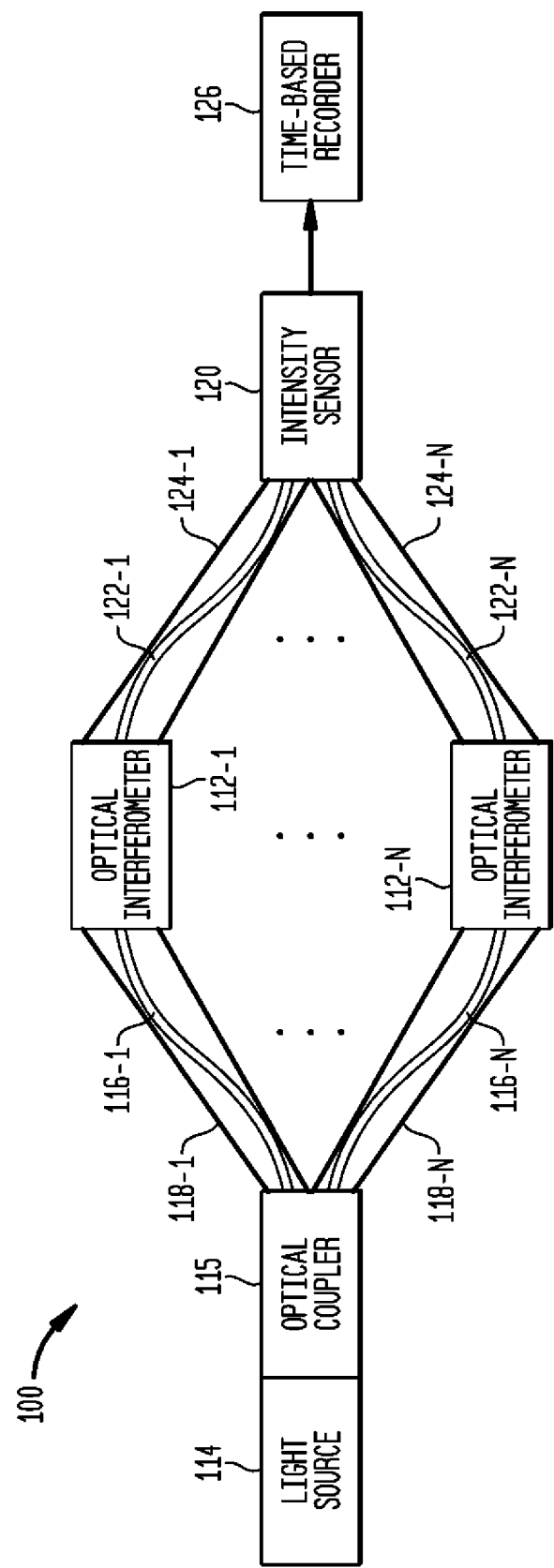
FIG. 2 is a block diagram of a gas detection and monitoring system configured for multiple-point gas detection in accordance with another embodiment of the present invention.

In the illustrated embodiment, the present invention is sensitive to gas pressure in the area of free beam path 12B. Since this will generally be a small area, the use of a single optical interferometer may not be able to adequately monitor a storage tank for leaks. To remedy this, the present invention can be expanded to utilize multiple optical interferometers with each such interferometer (with its free beam path) being placed at a unique monitoring location. Accordingly, FIG. 2 illustrates an example of such a multiple-point gas detection and monitoring system 100. In its illustrated configuration, system 100 has a plurality of optical interferometers 112-1, . . . , 112-N positioned at various locations in an environment of interest. Each optical interferometer defines a free beam path (not shown for sake of clarity) similar to free beam path 12B described above. A light source 114 generates light (e.g., a continuous wave laser beam) that is distributed to each optical interferometer 112-1, . . . , 112-N using an optical coupler 115 and corresponding plurality of single-mode optical fibers 116-1, . . . , 116-N. Optical coupler 115 is any optical beam splitter, switch, etc., that can be used in conjunction with source 114 and fibers 116-1, . . . , 116-N to deliver the laser light to each of interferometers 112-1, . . . , 112-N. Fibers 116-1, . . . , 116-N can be fixed in their orientations either individually or collectively. For example, the illustrated embodiment uses a corresponding plurality of housings 118-1, . . . , 118-N.

Each optical interferometer in system 100 functions as the above-described optical interferometer 12. Accordingly, each of interferometers 112-1, . . . , 112-N outputs light indicative of gas presence at its particular location in the environment of interest. Thus, output light from each interferometer 112-1, . . . , 112-N is guided to an intensity sensor 120 by one of corresponding single-mode optical fibers 122-1, . . . , 122-N, the orientations of which can be fixed individually (or collectively) by corresponding housings 124-1, . . . , 124-N. A time-base recorder 126 is used to record a time history of the output light associated with each of interferometers 112-1, . . . , 112-N.

The time history data provided by interferometers 112-1, . . . , 112-N can be used to comprehensively describe a gas leak. A leak's origin can be closely approximated by an analysis of the time history data. Further, the time history data could serve as data input for a processing scheme that approximates the actual leak location using, for example, triangulation routines.

Figure 3:
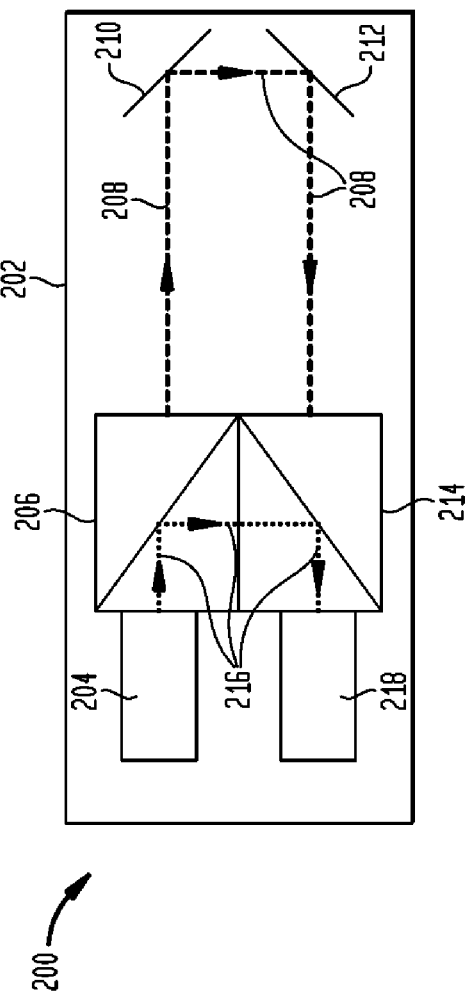
FIG. 3 is a schematic view of a Michelson solid-body optical interferometer in accordance with an embodiment of the present invention.

As mentioned above, the particular type of optical interferometer used is not a limitation of the present invention. One type of interferometer that lends itself to compact, solid-body optics construction is a Michelson interferometer. By way of example, one suitable solid body Michelson interferometer is illustrated in FIG. 3 and is referenced generally by numeral 200. Interferometer 200 has a rigid planar base 202 with a number of optical components mounted thereon. Specifically, a first "gradient-index" (GRIN) lens 204 is coupled to a first beam splitter 206. Light enters interferometer 200 via GRIN lens 204, i.e., via a single-mode optical fiber (not shown) coupled thereto. One output of beam splitter 206 starts a free beam path (i.e., the dashed-line path referenced by numeral 208) that traces a path to/between mirrors 210/212 and then on to a second beam splitter 214. Beam splitters 206 and 214 are configured and arranged to also define a reference path (i.e., the dotted-line path referenced by arrow 216) therethrough that is indicative of the light entering GRIN lens 204. Beam splitter 216 combines the light at the end of the interferometer's free beam path with the light on reference path 216. The naturally-interfering output light exits beam splitter 216 and is coupled to a second GRIN lens 218 where a single-mode optical fiber (not shown) can be coupled.

Figure 4:
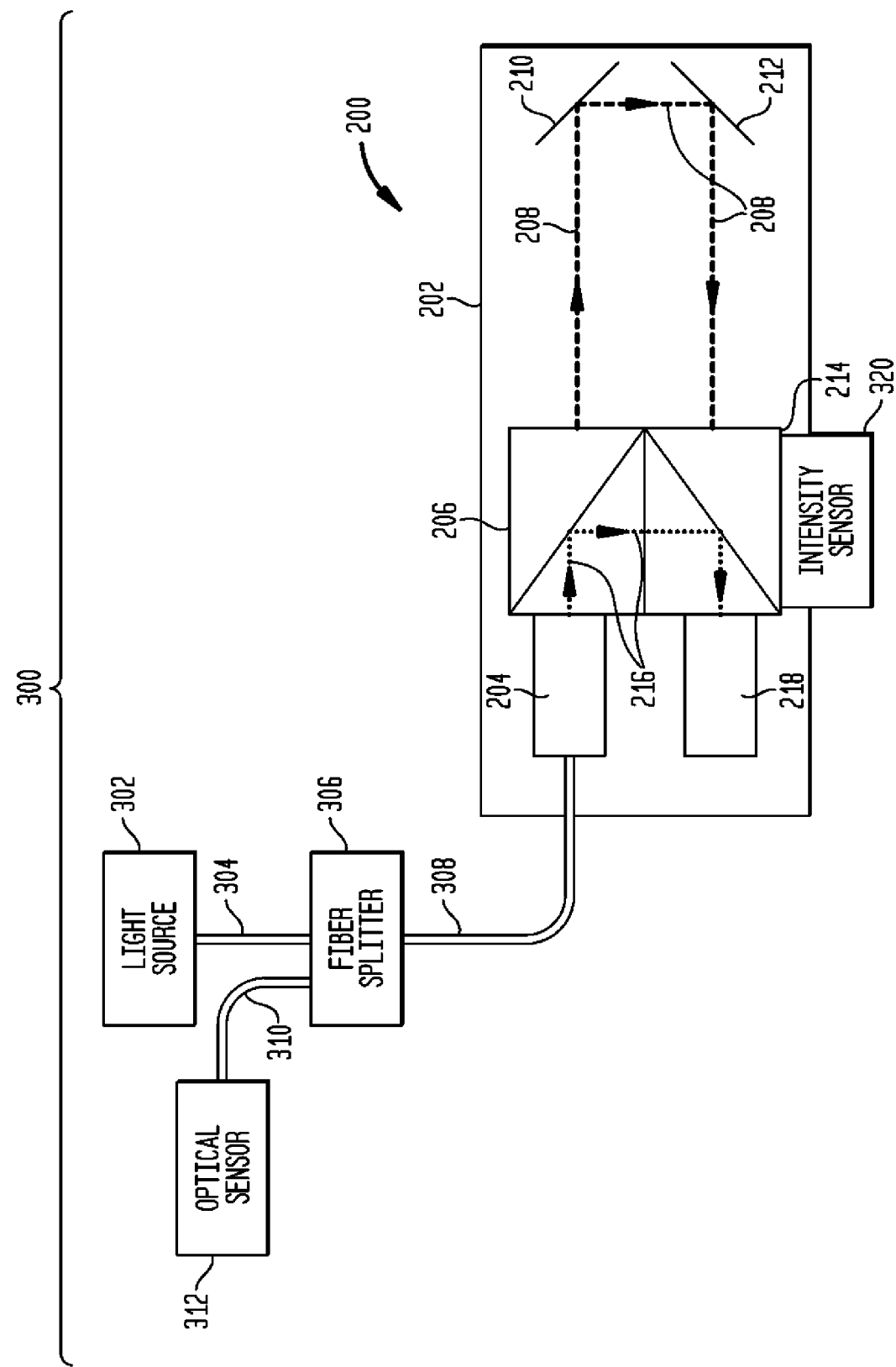
FIG. 4 is a schematic view of a gas detection and monitoring system that also detects background noise in accordance with another embodiment of the present invention.

Referring again to FIG. 1, the use of housings 18 and 24 greatly reduce the effects of vibrations on the single-mode optical fibers used solely as light conduits in the present invention. However, since it may be impossible to eliminate all vibration effects on the optical fibers, the present invention can also be configured to detect noise caused by such vibration effects. This noise can then be readily "subtracted" from the signal of interest, i.e., an interferometer's output light. One example of a gas detection and monitoring system configured for detection of background noise is illustrated in FIG. 4 and is referenced generally by numeral 300 where common reference numerals will be used for elements previously described herein. System 300 is utilizing interferometer 200 described above. A light beam is provided to GRIN lens 204 by means of a light source 302, a single-mode optical fiber 304, a fiber splitter 306, and a single-mode optical fiber 308. More specifically, fiber 304 guides light to splitter 306 where the light is split into two paths, only one of which is needed and is defined by optical fiber 308. Light carried by optical fiber 308 is coupled into GRIN lens 204. As would be understood in the art, a portion of the light incident on GRIN lens 204 is reflected back along fiber 308 to splitter 306. This reflected light is directed by splitter 306 and optical fiber 310 to an optical sensor (e.g., a photodiode). The reflected light signal is indicative of any vibration "noise" picked up along the light delivery path defined by fiber 304/splitter 306/fiber 308. The operation of interferometer 200 is the same as described above. To eliminate the need for optical fibers on the output side of interferometer 200, an intensity sensor 320 can be coupled directly to the output side of beam splitter 214. The noise signal detected by sensor 312 can be subtracted from the signal (which is inclusive of a signal-of-interest plus noise) detected by sensor 320.

The advantages of the present invention are numerous. The system/method described herein can be used in vacuum environments (e.g., space) to detect/monitor gas presence over long time periods. The system/method is readily adapted to monitor multiple points simultaneously. The resulting data set can be used in manual or automated analysis schemes to comprehensively evaluate gas presence in an environment of interest. The system/method utilize simple yet rugged components that can withstand the rigors of a space deployment. The pairing of a CW laser and a single-mode optical fiber reduces the overall size of the system while simplifying and improving the detection and measurement of optical interference indicative of a gas leak in a vacuum environment such as space.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A system for detecting and monitoring the presence of a gas, comprising:
    a source generating a light beam;
    an optical interferometer defining a free-space optical path disposed in an environment of interest;
    an optical detector;
    a single-mode optical fiber coupled between said source and said optical interferometer, wherein said light beam incident on said optical interferometer is guided to said optical path and traverses therealong to an end of said optical path, wherein said light beam guided to said optical path is combined with said light beam at said end of said optical path to define an output light;
    said optical detector optically coupled to said optical interferometer wherein said output light is guided to said optical detector; and
    means coupled to said optical detector for recording a temporal history of said output light.

2. A system as in claim 1, further comprising a second single-mode optical fiber coupled between said optical interferometer and said optical detector, wherein said output light is guided to said optical detector.

3. A system as in claim 2, further comprising means for fixing orientations of said single-mode optical fiber and said second single-mode optical fiber.

4. A system as in claim 1, wherein said optical interferometer is selected from the group consisting of a Fabry-Perot interferometer, a Mach-Zehnder interferometer, and a Michelson interferometer.

5. A system as in claim 1, wherein said optical interferometer comprises a solid-body optical interferometer.

6. A system as in claim 1, wherein said source is a continuous wave laser.

7. A system as in claim 1, further comprising means for fixing an orientation of said single-mode optical fiber.

8. A system as in claim 1, wherein a portion of said light beam incident on said optical interferometer is back-reflected therefrom into said single-mode optical fiber, said system further comprising detection means coupled to said single-mode optical fiber for detecting said portion of said light beam.

9. A method of detecting and monitoring the presence of a gas, comprising the steps of:
    generating a light beam;
    disposing a free-space optical path of an optical interferometer in an environment of interest;
    guiding said light beam to the optical interferometer using a single-mode optical fiber wherein said light beam traverses along said optical path to an end thereof;
    combining said light beam guided to said optical path with said light beam at said end of said optical path to define an output light;
    guiding said output light to an optical detector; and
    recording a temporal history of said output light.

10. A method according to claim 9, wherein the environment of interest is space.

11. A method according to claim 9, wherein the environment of interest is a vacuum.

12. A method according to claim 9, wherein the optical interferometer is selected from the group consisting of a Fabry-Perot interferometer, a Mach-Zehnder interferometer, and a Michelson interferometer.

13. A method according to claim 9, wherein the optical interferometer is a solid-body optical interferometer.

14. A method according to claim 9, wherein said light beam comprises a continuous wave laser beam.

15. A method according to claim 9, further comprising the step of fixing an orientation of the single-mode optical fiber.

16. A method according to claim 9, wherein a portion of said light beam incident on the optical interferometer is back-reflected therefrom into the single-mode optical fiber, said method further comprising the step of detecting said portion of said light beam.

17. A system for detecting and monitoring the presence of a gas, comprising:
- a laser source generating laser light;
- a plurality of optical interferometers distributed in an environment of interest, each of said optical interferometers defining a free-space optical path disposed in a region of the environment of interest;
- a corresponding plurality of optical detectors;
- first means coupled between said laser source and each of said optical interferometers wherein, for each of said optical interferometers, said laser light is guided to said optical path associated therewith by said first means and traverses therealong to an end of said optical path associated therewith, and wherein each of said optical interferometers combines said laser light guided to said optical path associated therewith said laser light at said end of said optical path associated therewith to define an output light associated therewith;
- second means coupled between each of said optical interferometers and a corresponding one of said optical detectors, wherein each said output light is guided by said second means to said corresponding one of said optical detectors; and
- means coupled to each of said optical detectors for recording a temporal history of each said output light.

18. A system as in claim 17, wherein each of said optical interferometers is selected from the group consisting of a Fabry-Perot interferometer, a Mach-Zehnder interferometer, and a Michelson interferometer.

19. A system as in claim 17, wherein each of said optical interferometers comprises a solid-body optical interferometer.

20. A system as in claim 17, wherein said laser source is a continuous wave laser.

21. A system as in claim 17, further comprising means for fixing orientations of said first means and said second means.

22. A method of detecting and monitoring the presence of a gas, comprising the steps of:
- generating laser light;
- distributing a plurality of optical interferometers in an environment of interest, each of said optical interferometers defining a free-space optical path in a region of the environment of interest;
- guiding said laser light to each of the optical interferometers using a first single-mode optical fiber wherein, for each of the optical interferometers, said laser light traverses along said optical path associated therewith to an end thereof, and wherein each of the optical interferometers combines said laser light guided to said optical path associated therewith said laser light at said end of said optical path associated therewith to define an output light associated therewith;
- guiding each said output light to an optical detector using a second single-mode optical fiber; and
- recording a temporal history of each said output light.

23. A method according to claim 22, wherein the environment of interest is space.

24. A method according to claim 22, wherein the environment of interest is a vacuum.

25. A method according to claim 22, wherein each of the optical interferometers is selected from the group consisting of a Fabry-Perot interferometer, a Mach-Zehnder interferometer, and a Michelson interferometer.

26. A method according to claim 22, wherein each of the optical interferometers is a solid-body optical interferometer.

27. A method according to claim 22, wherein said laser light comprises a continuous wave of optical energy.

28. A method according to claim 22, further comprising the step of fixing orientations of the first single-mode optical fiber and the second single-mode optical fiber.

* * * * *